United States Patent
Saito

(10) Patent No.: US 8,367,583 B2
(45) Date of Patent: Feb. 5, 2013

(54) COMPOSITION AND METHOD FOR CONTROLLING PESTS

(75) Inventor: Shigeru Saito, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/321,591

(22) PCT Filed: May 21, 2010

(86) PCT No.: PCT/JP2010/059055
§ 371 (c)(1), (2), (4) Date: Jan. 11, 2012

(87) PCT Pub. No.: WO2010/137676
PCT Pub. Date: Dec. 2, 2010

(65) Prior Publication Data
US 2012/0115721 A1    May 10, 2012

(30) Foreign Application Priority Data

May 25, 2009  (JP) ................................. 2009-125903
Jul. 2, 2009   (JP) ................................. 2009-158118
Feb. 22, 2010  (JP) ................................. 2010-036393

(51) Int. Cl.
*A01N 43/56* (2006.01)
*A01N 47/02* (2006.01)
*A01N 37/30* (2006.01)
*A01P 7/00* (2006.01)
*A01P 7/02* (2006.01)
*A01P 7/04* (2006.01)

(52) U.S. Cl. ........ 504/100; 504/147; 504/322; 514/407; 514/563

(58) Field of Classification Search .................. 504/100, 504/147, 322; 514/407, 563
See application file for complete search history.

(56) References Cited

U.S. PATENT DOCUMENTS

| 8,093,185 B2 * | 1/2012 | Silverman et al. ............ 504/321 |
| 2002/0065228 A1 | 5/2002 | Linderman et al. |
| 2003/0134857 A1 | 7/2003 | Uhr et al. |
| 2010/0048397 A1 | 2/2010 | Lewis |

FOREIGN PATENT DOCUMENTS

| JP | 59-039803 | 3/1984 |
| JP | 11-158131 | 6/1999 |
| JP | 11-255607 | 9/1999 |
| JP | 2007-262072 | 10/2007 |
| JP | 2009-502826 | 1/2009 |
| WO | 2007-017040 | 2/2007 |
| WO | 2009/055044 | 4/2009 |

OTHER PUBLICATIONS

International Search Report issued Jul. 13, 2010 in International (PCT) Application No. PCT/JP2010/059055 along with the Written Opinion.

* cited by examiner

*Primary Examiner* — John Pak
(74) *Attorney, Agent, or Firm* — Wenderoth, Lind & Ponack, L.L.P.

(57) ABSTRACT

The present invention provides a composition comprising, as active ingredients, 4-oxo-4-[(2-phenylethyl)amino]-butyric acid and fipronil; a method of controlling pests, which comprises applying effective amounts of 4-oxo-4-[(2-phenylethyl)amino]-butyric acid and fipronil to a plant or growing site of plant and so on.

8 Claims, No Drawings

US 8,367,583 B2

COMPOSITION AND METHOD FOR CONTROLLING PESTS

This application is a U.S. national stage of International Application No. PCT/JP2010/059055 filed May 21, 2010.

TECHNICAL FIELD

The present invention relates to a composition and a method for controlling pests.

BACKGROUND ART

Conventionally, 4-oxo-4-[(2-phenylethyl)amino]-butyric acid has been known as an active ingredient for plant growth regulator (Japanese Patent No. 4,087,942). Fipronil [chemical name: 5-amino-1-(2,6-dichloro-α,α,α-trifluoro-p-tolyl)-4-trifluoromethylsulfinyl pyrazole-3-carbonitrile] has been known as an active ingredient for pesticide (WO87/03781).

DISCLOSURE OF INVENTION

An object of the present invention is to provide a composition for controlling pests having excellent control efficacy for pests and a method effective for controlling pests.

The present invention provides a composition for controlling pests and a method for controlling pests, in which control efficacy for pests has been increased by the combined use of 4-oxo-4-[(2-phenylethyl)amino]-butyric acid and fipronil.

Specifically, the present invention takes the following constitutions:

[1] A composition for controlling pests comprising, as active ingredients, 4-oxo-4-[(2-phenylethyl)amino]-butyric acid and fipronil;
[2] The composition for controlling pests according to [1], wherein a weight ratio of 4-oxo-4-[(2-phenylethyl)amino]-butyric acid to fipronil is in the range of 1:99 to 99:1;
[3] A seed treatment agent comprising, as active ingredients, 4-oxo-4-[(2-phenylethyl)amino]-butyric acid and fipronil;
[4] A plant seed treated with effective amounts of 4-oxo-4-[(2-phenylethyl)amino]-butyric acid and fipronil;
[5] A method of controlling pests, which comprises applying effective amounts of 4-oxo-4-[(2-phenylethyl)amino]-butyric acid and fipronil to a plant or growing site of plant;
[6] The method of controlling pests according to [5], wherein the plant is seed or seedling;
[7] The method of controlling pests according to [5], wherein the plant is a sugarcane stem cutting;
[8] The method of controlling pests according to [5], wherein the growing site of plant is soil before or after planting the plant on it; and
[9] Combined use of 4-oxo-4-[(2-phenylethyl)amino]-butyric acid and fipronil for controlling pests.

The composition of the present invention exerts excellent control efficacy against pests.

MODE FOR CARRYING OUT THE INVENTION

The composition of the present invention comprises, as active ingredients, 4-oxo-4-[(2-phenylethyl)amino]-butyric acid (hereinafter, referred to as the compound I in some cases) and fipronil. Since the control efficacy against pests has been increased by using 4-oxo-4-[(2-phenylethyl)amino]-butyric acid in combination with fipronil in the pesticidal composition of the present invention, it can exert sufficient control efficacy in a lower chemical amount as compared with the case of fipronil being used singly.

The compound I, 4-oxo-4-[(2-phenylethyl)amino]-butyric acid, is a compound described in Japanese Patent No. 4,087,942 and can be produced, for example, by the method described in the publication.

The compound I, 4-oxo-4-[(2-phenylethyl)amino]-butyric acid, may be a salt with a base. Examples of the basic salt of 4-oxo-4-[(2-phenylethyl)amino]-butyric acid include the followings:

metal salts such as alkali metal salts and alkali earth metal salts (for example, salts of sodium, potassium or magnesium);
salts with ammonia; and
salts with organic amines such as morpholine, piperidine, pyrrolidine, mono lower alkylamine, di lower alkylamine, tri lower alkylamine, monohydroxy lower alkylamine, dihydroxy lower alkylamine and trihydroxy lower alkylamine.

Fipronil is a compound described in WO87/03781 and can be produced, for example, by the method described in the publication.

While the composition of the present invention may be a simple mixture of the compound I and fipronil, it may be prepared by mixing the compound I, fipronil and an inert carrier, and adding to the mixture a surfactant or other adjuvants as needed so that the mixture can be used as such a formulation as emulsifiable concentrate, liquid agent, microemulsion, flowable agent, oil agent, wettable powder, granulated wettable powder, water soluble powder, dust formulation, granule, microgranule, seed-coating agent, seed-soaking agent, smoking agent, tablet, microcapsule, spray, aerosol, carbon dioxide gas preparation, EW agent, trunk injection and trunk-coating agent. The composition of the present invention can be used as a root growth promoter, pesticide or seed treatment agent as it is or with the addition of other inert ingredients.

Examples of the solid carrier (dilution agent, extending agent) which can be used in the preparations include fine powders or granules such as plant powders (for example, soybean flour, tobacco flour, wheat flour, wood flour and so on), mineral powders (for example, clays such as kaolin clay, Fubasami clay, bentonite and acid clay, talcs such as talc powder and agalmatolite powder, silicas such as diatomaceous earth and mica powder, and so on), synthetic hydrated silicon oxide, alumina, talc, ceramic, other inorganic minerals (sericite, quartz, sulfur, active carbon, calcium carbonate, hydrated silica and so on) and chemical fertilizers (ammonium sulfate, ammonium phosphate, ammonium nitrate, urea, ammonium chloride). One or more (preferably, one or more and three or less) of these solid carriers may be mixed at suitable proportion and used.

Examples of the liquid carrier include water, alcohols (for example, methyl alcohol, ethyl alcohol, n-propyl alcohol, isopropyl alcohol, butyl alcohol, hexyl alcohol, benzyl alcohol, ethylene glycol, propylene glycol, phenoxyethanol and so on), ketones (for example, acetone, methyl ethyl ketone, methyl isobutyl ketone, cyclohexanone and so on), ethers (for example, diisopropyl ether, 1,4-dioxane, tetrahydrofuran, ethylene glycol monomethyl ether, ethylene glycol dimethyl ether, diethylene glycol monomethyl ether, propylene glycol monomethyl ether, dipropylene glycol monomethyl ether, 3-methoxy-3-methyl-1-butanol and so on), aliphatic hydrocarbons (for example, hexane, cyclohexane, kerosene, lamp oil, fuel oil, machine oil and so on), aromatic hydrocarbons (for example, toluene, xylene, ethylbenzene, dodecylbenzene, phenylxylylethane, solvent naphtha, methylnaphthalene and so on), halogenated hydrocarbons (for example, dichloromethane, trichloroethane, chloroform, carbon tetrachloride and so on), acid amides (for example, N,N-dimethylformamide, N,N-dimethylacetamide, N-methylpyrrolidone, N-octylpyrrolidone and so on), esters (for example, butyl lactate, ethyl acetate, butyl acetate, isopropyl myristate, ethyl oleate, diisopropyl adipate, diisobutyl adipate, propylene glycol monomethyl ether acetate, fatty acid glycerin ester, γ-butyrolactone and so on), nitriles (for example, acetonitrile, isobutyronitrile, propionitrile and so on), carbonates (for example, propylene carbonate and so on), and vegetable oils (for example, soybean oil, olive oil, linseed oil, coconut oil, palm oil, peanut oil, malt oil, almond oil, sesame oil, mineral oil, rosmarinic oil, geranium oil, rapeseed oil, cotton seed oil, corn oil, safflower oil, orange oil and so on). One or more (preferably, one or more and three or less) of these liquid carriers may be mixed at suitable proportion and used.

Examples of the gaseous carrier include fluorocarbon, butane gas, LPG (liquefied petroleum gas), dimethyl ether and carbon dioxide gas. These gaseous carriers can be used singly or two of them can be mixed in suitable proportion, or can be combined with a suitable liquid carrier, and used.

Examples of the surfactant include nonionic and anionic surfactants such as soaps, polyoxyethylene alkyl aryl ethers (for example, Noigen (product name, registered trademark, manufactured by Dai-Ichi Kogyo Seiyaku Co., Ltd.), EA142 (EA142(product name, manufactured by Dai-Ichi Kogyo Seiyaku Co., Ltd.)), Nonal (product name, manufactured by Toho Chemical Industry Co., Ltd.)), alkylsulfates (for example, Emal 10 (product name, registered trademark, manufactured by Kao Corporation), Emal 40 (product name, registered trademark, manufactured by Kao Corporation)), alkylbenzene sulfonates (for example, Neogen (product name, registered trademark, manufactured by Dai-Ichi Kogyo Seiyaku Co., Ltd.), Neogen T (product name, registered trademark, manufactured by Dai-Ichi Kogyo Seiyaku Co., Ltd.), Neopelex (product name, registered trademark, manufactured by Kao Corporation), polyethylene glycol ethers (for example, Nonipole 85 (product name, registered trademark, manufactured by Sanyo Chemical Industries, Ltd.), Nonipole 100 (product name, registered trademark, manufactured by Sanyo Chemical Industries, Ltd.), Nonipole 160 (product name, registered trademark, manufactured by Sanyo Chemical Industries, Ltd.)), polyoxyethylene alkyl ethers (for example, Noigen ET-135 (product name, registered trademark, manufactured by Dai-Ichi Kogyo Seiyaku Co., Ltd.)), polyoxyethylene polyoxypropylene block polymers (for example, Newpole PE-64 (product name, registered trademark, manufactured by Sanyo Chemical Industries, Ltd.)), polyhydric alcohol esters (for example, Tween 20 (product name, registered trademark, manufactured by Kao Corporation), Tween 80 (product name, registered trademark, manufactured by Kao Corporation)), alkylsulfosuccinates (for example, Sanmorin OT20 (product name, registered trademark, manufactured by Sanyo Chemical Industries, Ltd.), Newcalgen EX70 (product name, manufactured by TAKEMOTO Oil & Fat Co., Ltd.)), alkyl naphthalene sulfonates (for example, Newcalgen WG-1 (product name, manufactured by TAKEMOTO Oil & Fat Co., Ltd.), and alkenyl sulfonates (for example, Sorpole 5115 (product name, registered trademark, manufactured by Toho Chemical Industry Co., Ltd.)). One or more (preferably, one or more and three or less) of these surfactants can be mixed in suitable proportion and used.

Examples of the other additives include casein, gelatin, saccharides (starch, xanthan gum, gum arabic, cellulose derivatives, alginic acid and so on), lignin derivatives, bentonite, synthetic water-soluble polymers (polyvinyl alcohol, polyvinyl pyrrolidone, polyacrylic acids and so on), PAP (acidic isopropyl phosphate), BHT (2,6-di-tert-butyl-4-methylphenol), and BHA (mixture of 2-tert-butyl-4-methoxyphenol and 3-tert-butyl-4-methoxyphenol).

In the pesticidal composition of the present invention, the weight ratio of the compound I to fipronil is typically in the range of 1:99 to 99:1, preferably 10:90 to 99:1, more preferably 10:90 to 90:10. When the composition of the present invention is applied as a foliar spray, the weight ratio is typically in the range of 1:99 to 99:1, preferably 10:90 to 90:10. When used as a seed treatment agent, the weight ratio is typically in the range of 1:99 to 99:1, preferably 10:90 to 99:1, more preferably 10:90 to 90:10.

In the composition of the present invention, the total amount of the compound I and fipronil (hereinafter referred to as the amount of the active ingredients) is typically within a range from 0.01 to 95% by weight, preferably from 0.1 to 80% by weight, and more preferably from 1 to 50% by weight. When the composition of the present invention is prepared into emulsifiable concentrate, liquid agent or wettable powder such as granulated wettable powder, the amount of the active ingredients is typically within a range from 1 to 90% by weight, preferably from 1 to 80% by weight, and more preferably from 5 to 60% by weight. When the composition of the present invention is prepared into oil agent or dust formulation, the amount of the active ingredients is typically within a range from 0.01 to 90% by weight, preferably from 0.1 to 50% by weight, and more preferably from 0.1 to 20% by weight. When the composition of the present invention is prepared into granule, the amount of the active ingredients is typically within a range from 0.1 to 50% by weight, preferably from 0.5 to 50% by weight, and more preferably from 1 to 20% by weight.

In the pesticidal composition of the present invention, the content of a liquid carrier or a solid carrier is, for example, within a range from 1 to 90% by weight, and preferably from 1 to 70% by weight, and the content of a surfactant is, for example, within a range from 1 to 20% by weight, and preferably from 1 to 15% by weight. When the pesticidal composition of the present invention is prepared into liquid agent, the content of water is, for example, from 20 to 90% by weight and the content of the surfactant is from 1 to 20% by weight, and preferably from 1 to 10% by weight.

The pesticidal composition of the present invention can protect plants from damages by the following pests (for example, harmful arthropods such as harmful insects and harmful mites) which cause damages such as feeding and sucking to plants. Examples of the pests against which the composition of the present invention has control efficacy include the followings.

Hemiptera: planthoppers such as small brown planthopper (*Laodelphax striatellus*), brown rice planthopper (*Nilaparvata lugens*) and white-backed rice planthopper (*Sogatella furcifera*); leafhoppers such as green rice leafhopper (*Nephotettix cincticeps*) and green rice leafhopper (*Nephotettix virescens*); aphids such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*) and tropical citrus aphid (*Toxoptera citricidus*); stink bugs such as green stink bug (*Nezara antennata*), bean bug (*Riptortus clavetus*), rice bug (*Leptocorisa chinensis*), white spotted spined bug (*Eysarcoris parvus*), brown marmorated stink bug (*Halyomorpha mista*) and tarnished plant bug (*Lygus lineolaris*); whiteflies such as greenhouse whitefly (*Trialeurodes vaporariorum*), sweetpotato whitefly (*Bemisia tabaci*) and silverleaf whitefly (*Bemisia argentifolii*); scales such as california red scale (*Aonidiella*

*aurantii*), san Jose scale (*Comstockaspis perniciosa*), citrus snow scale (*Unaspis citri*), red wax scale (*Ceroplastes rubens*) and cottony cushion scale (*Icerya purchasi*); lace bugs; psyllids;

Lepidoptera: pyralid moths such as rice stem borer, (*Chilo suppressalis*), yellow stem borer (*Tryporyza incertulas*), rice leafroller (*Cnaphalocrocis medinalis*), cotton leafroller (*Notarcha derogata*), indian meal moth (*Plodia interpunctella*), oriental corn borer (*Ostrinia furnacalis*), european corn borer (*Ostrinia nubilaris*), cabbage webworm (*Hellula undalis*) and bluegrass webworm (*Pediasia teterrellus*); owlet moths such as common cutworm (*Spodoptera litura*), beet armyworm (*Spodoptera exigua*), rice armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; Pieridae such as cabbage butterfly (*Pieris rapae*); tortricid moths such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners such as tea leafroller (*Caloptilia theivora*), and apple leafminer (*Phyllonorycter ringoneella*); fruitworm moths such as peach fruit moth (*Carposina niponensis*); lyonetiid moths such as *Lyonetia* spp.; tussock moths such as *Lymantria* spp., and *Euproctis* spp.; yponomeutid moths such as diamondback moths (*Plutella xylostella*); gelechiid moths such as pink bollworm (*Pectinophora gossypiella*), and potato tubeworm (*Phthorimaea operculella*); tiger moths such as fall webworm (*Hyphantria cunea*); tineid moths such as casemaking clothes moth (*Tinea translucens*), and webbing clothes moth (*Tineola bisselliella*);

Thysanoptera: thrips (*Thripidae*) such as yellow citrus thrip (*Frankliniella occidentalis*), melon thrip (*Thrips parmi*), yellow tea thrip (*Scirtothrips dorsalis*), onion thrip (*Thrips tabaci*), flower thrip (*Frankliniella intonsa*), tobacco thrip (*Frankliniella fusca*);

Diptera: leaf miners such as oriental house fly (*Musca domestica*), common house mosquito (*Culex pipiens pallens*), common horse fly (*Tabanus trigonus*), onion maggot (*Hylemya antiqua*), seedcorn maggot (*Hylemya platura*), hyrcanus group mosquito (*Anopheles sinensis*), rice leafminer (*Agromyza oryzae*), rice leafminer (*Hydrellia griseola*), rice stem maggot (*Chlorops oryzae*) and legume leafminer (*Liriomyza trifolii*); melon fly (*Dacus cucurbitae*), Mediterranean fruit fly (*Ceratitis capitata*);

Coleoptera: twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*);

Orthoptera: Asiatic locust (*Locusta migratoria*), African mole cricket (*Gryllotalpa africana*), rice grasshopper (*Oxya yezoensis*), rice grasshopper (*Oxya japonica*);

Hymenoptera: Cabbage sawfly (*Athalia rosae*), leaf-cutting ant (*Acromyrmex* spp.), fire ant (*Solenopsis* spp.);

Blattaria: German cockroach (*Blattella germanica*), smokybrown cockroach (*Periplaneta fuliginosa*), american cockroach (*Periplaneta americana*), brown cockroach (*Periplaneta brunnea*) and oriental cockroach (*Blatta orientalis*);

Acarina: spider mites such as two-spotted spider mite (*Tetranychus urticae*), citrus red mite (*Panonychus citri*), and *Oligonychus* spp.; eriophyid mites such as pink citrus rust mite (*Aculops pelekassi*); tarosonemid mites such as broad mite (*Polyphagotarsonemus latus*); false spider mites; peacock mites; flour mites such as mould mite (*Tyrophagus putrescentiae*); house dust mites such as American house dust mite (*Dermatophagoides farinae*), European house dust mite (*Dermatophagoides ptrenyssnus*); cheyletid mites such as *Cheyletus eruditus, Cheyletus malaccensis, Cheyletus moorei;*

Nematodes: rice white-tip nematode (*Aphelenchoides besseyi*), strawberry bud nematode (*Nothotylenchus acris*).

Pests can be controlled by applying effective amounts of the compound I and fipronil to the pests or a place where the pests inhabit or a place where the pests may inhabit such as plant or soil.

By applying effective amounts of the compound I and fipronil to plants or growing sites of plants, pests can be controlled. Examples of a plant which is the object of the application include foliages, seeds, bulbs and seedlings. As used herein, the bulb means a bulb, corm, rhizoma, stem tuber, root tuber and rhizophore. In the present specification, the seedling includes cutting and sugarcane stem cutting. Examples of the growing sites of plants include soil before or after planting plants.

When the application is conducted to pests of plant, a plant or growing site of plant, the compound I and fipronil may be separately applied for the same period, but they are typically applied as the pesticidal composition of the present invention for simplicity of the application.

Specific examples of the method of controlling pests according to the present invention include treatment of foliage of plants, such as foliage application; treatment to cultivation lands of plants, such as soil treatment; treatment of seeds, such as seed sterilization and seed coating; treatment of seedlings; and treatment of bulbs such as seed tuber.

Specific examples of the treatment of foliage of plants in the controlling method of the present invention include treatment methods of applying to surfaces of plants, such as foliage spraying and trunk spraying. The active ingredients may be directly applied to plants before transplantation, and examples of the treatment method of directly absorbing to the plants include a method of soaking entire plants or roots. A formulation obtained by using a solid carrier such as a mineral powder may be adhered to the roots.

Examples of the soil treatment method in the controlling method of the present invention include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray and seedbed. Examples of the treating period include before seeding, at the time of seeding, immediately after seeding, raising period, before settled planting, at the time of settled planting, and growing period after settled planting. In the above soil treatment, active ingredients may be simultaneously applied to the plant, or a solid fertilizer such as a paste fertilizer containing active ingredients may be applied to the soil. Also active ingredients may be mixed in an irrigation liquid, and examples thereof include injecting to irrigation facilities such as irrigation tube, irrigation pipe and sprinkler, mixing into flooding liquid between furrows and mixing into culture solution. Alternatively, an irrigation liquid is mixed with active ingredients in advance and, for example, used for treatment by an appropriate irrigating method including the irrigating method mentioned above and the other methods such as sprinkling and flooding.

Examples of the method of treating seeds or bulbs in the controlling method of the present invention include a method of treating seeds or bulbs of plants to be protected from pests with the pesticidal composition of the present invention, and specific examples thereof include a spraying treatment in which a suspension of the pesticidal composition of the present invention is atomized and sprayed over surfaces of seeds or bulbs, an smearing treatment in which a wettable powder, an emulsifiable concentrate or a flowable agent of the pesticidal composition of the present invention is applied to seeds or bulbs with a small amount of water added or without dilution, an immersing treatment in which seeds are immersed in a solution of the pesticidal composition of the present invention for a certain period of time, a film coating treatment, and a pellet coating treatment.

Examples of the method of treating seedling in the control method of the present invention include a spraying treatment in which a dilution prepared by diluting the pesticidal composition of the present invention with water so as to have a suitable concentration of the active ingredients is sprayed on the entire seedling; an immersing treatment in which a seedling is immersed in the dilution; and an application treatment in which the pesticidal composition of the present invention formulated into a dust formulation is adhered on the entire seedling. Examples of the treatment of soil before or after planting seedlings include a method in which a dilution prepared by diluting the pesticidal composition of the present invention with water so as to have a suitable concentration of the active ingredients is sprayed on the seedling and the soil around the seedling after planting the seedling; and a method in which the pesticidal composition of the present invention formulated into a solid formulation such as a granulate or a dust formulation is sprayed on the soil around the seedling after planting the seedling.

Examples of the method of treating sugarcane in the control method of the present invention include a spraying treatment in which a dilution prepared by diluting the pesticidal composition of the present invention with water so as to have a suitable concentration of the active ingredients is sprayed on the entire sugarcane stem cutting; an immersing treatment in which a sugarcane stem cutting is immersed in the dilution; and an application treatment in which the pesticidal composition of the present invention formulated into a dust formulation is adhered on the entire sugarcane stem cutting. Examples of the treatment of soil before or after planting sugarcane stem cutting include a method in which a dilution prepared by diluting the pesticidal composition of the present invention with water so as to have a suitable concentration of the active ingredients is sprayed on the sugarcane stem cutting and the soil around the cutting after planting the cutting and before covering it by soil; a method in which the dilution is sprayed onto the surface of soil after planting the sugarcane stem cutting and covering it by the soil; and a method in which the pesticidal composition of the present invention formulated into a solid formulation such as a granulate or a dust formulation is sprayed on the sugarcane stem cutting and the soil around the cutting after planting the cutting and before covering it by soil; and a method in which the solid-formulated pesticidal composition is sprayed onto the surface of soil after planting the sugarcane stem cutting and covering it by the soil.

When a plant or a growing site of plants is treated with the compound I and fipronil, the amounts of the compound I and fipronil used for the treatment may be changed depending on the kind of the plant to be treated, the kind and the occurring frequency of the pests to be controlled, formulation form, treatment period, climate condition and so on, but the amount of the active ingredients per 1,000 $m^2$ is typically within a range from 0.1 to 2,000 g, and preferably from 10 to 1000g. In the case of soil treatment, the amount of the active ingredients per 1,000 $m^2$ is typically 0.1 to 2,000 g and preferably 1 to 1,000 g.

The emulsifiable concentrate, wettable powder, flowable agent and microcapsule are typically diluted with water, and then sprinkled for the treatment. In these cases, the total concentration of the compound I and fipronil is typically within a range from 1 to 20,000 ppm, and preferably from 10 to 1,000 ppm. The dust formulation and granule are typically used for the treatment without being diluted.

In the treatment of seeds, the amount of the active ingredients per one seed is typically within a range from 0.01 to 10 mg, and preferably 0.1 to 5 mg. The amount of the active ingredients per 100 kg of seeds is typically within a range from 1 to 300 g, and preferably from 5 to 100 g.

In the treatment of seedlings, the amount of the active ingredients per one seedling is typically within a range from 0.1 to 20 mg, and preferably from 1 to 10 mg. In the treatment of the soil before or after planting seedlings, the amount of the active ingredients per 1,000 $m^2$ is typically within a range from 0.1 to 100 g, and preferably from 1 to 50 g.

In the treatment of sugarcane, the amount of the active ingredients per one sugarcane stem cutting is typically within a range from 0.1 to 100 mg, and preferably from 1 to 50 mg. In the treatment of the soil before or after planting sugarcane stem cutting, the amount of the active ingredients per 1,000 $m^2$ is typically within a range from 0.1 to 400 g, and preferably from 1 to 200 g.

The controlling method of the present invention can be used in agricultural lands such as fields, paddy fields, lawns and orchards or in non-agricultural lands.

The present invention can be used in agricultural lands for cultivating the following "plant" and so on to promote root growth of the plants and so on.

Examples of the crops are as follows:

crops: corn, rice, wheat, barley, rye, oat, sorghum, cotton, soybean, peanut, buckwheat, beet, rapeseed, sunflower, sugarcane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, Dioscorea japonica, colocasia, etc.;

flowers;

foliage plants;

turf grasses;

fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, *macadamia* nuts, etc.), berries (blueberry, cranberry, blackberry, raspberry, etc.), grape, kaki fruit, olive, Japanese plum, banana, coffee, date palm, coconuts, etc.; and trees other than fruit trees; tea, mulberry, flowering plant, roadside trees (ash, birch, dogwood, Eucalyptus, *Ginkgo biloba*, lilac, maple, *Quercus*, poplar, Judas tree, Liquidambar formosana, plane tree, zelkova, Japanese arborvitae, fir wood, hemlock, juniper, *Pinus, Picea*, and Taxus cuspidate), etc.

The aforementioned "plants" include plants, to which tolerance to HPPD inhibitors such as isoxaflutole, ALS inhibitors such as imazethapyr and thifensulfuron-methyl, EPSP synthetase inhibitors such as glyphosate, glutamine synthetase inhibitors such as glufosinate, acetyl-CoA carboxylase inhibitors such as sethoxydim, and herbicides such as bromoxynil, dicamba and 2,4-D has been conferred by a classical breeding method or by genetic engineering techniques.

Examples of a "plant" on which tolerance has been conferred by a classical breeding method include rape, wheat, sunflower and rice tolerant to imidazolinone ALS inhibitory herbicides such as imazethapyr, which are already commercially available under a product name of Clearfield (registered trademark). Similarly, there is a soybean on which tolerance to sulfonylurea ALS inhibitory herbicides such as thifensulfuron-methyl has been conferred by a classical breeding method, which is already commercially available under a product name of STS soybean.

Examples of a plant on which tolerance to acetyl-CoA carboxylase inhibitors such as trione oxime or aryloxy phenoxypropionic acid herbicides has been conferred by a classical breeding method include SR corn. The plant on which tolerance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase tolerant to an acetyl-CoA carboxylase inhibitor is reported in Weed Science, vol. 53, pp. 728-746 (2005) and a plant tolerant to acetyl-CoA carboxylase inhibitors can be generated by introducing a gene of such an acetyl-CoA carboxylase variation into a plant by genetically engineering technology, or by introducing a variation conferring tolerance into a plant acetyl-CoA carboxylase.

Plants tolerant to acetyl-CoA carboxylase inhibitors or ALS inhibitors or the like can be generated by introducing into the plant cell a nucleic acid for introduction of base-substitution variation represented by Chimeraplasty Technique (Gura T. 1999. Repairing the Genome's Spelling Mistakes. Science 285: 316-318) to introduce a site-directed amino acid substitution variation into an acetyl-CoA carboxylase gene or an ALS gene of the plant.

Examples of a plant on which tolerance has been conferred by genetic engineering technology include corn, soybean, cotton, rape and sugar beet which are tolerant to glyphosate, and which have been commercially available under a product name of RoundupReady (registered trademark), AgrisureGT, and so on. There are corn, soybean, cotton and rape which are made tolerant to glufosinate by genetic engineering technology, which have been commercially available under a product name of LibertyLink (registered trademark). A cotton made tolerant to bromoxynil by genetic engineering technology has been commercially available under a product name of BXN.

The aforementioned "plants" include crops genetically engineered to be able to synthesize selective toxins as known in genus *Bacillus*.

Examples of toxins expressed in such genetically engineered crops include: insecticidal proteins derived from *Bacillus cereus* or *Bacillus popilliae*; δ-endotoxins derived from *Bacillus thuringiensis* such as Cry1Ab, Cry1Ac, Cry1F, Cry1Fa2, Cry2Ab, Cry3A, Cry3Bb1 or Cry9C; insecticidal proteins such as VIP1, VIP2, VIP3 or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, by using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, and so on.

Toxins contained in such genetically engineered plants are able to confer resistance particularly to insect pests belonging to Coleoptera, Hemiptera, Diptera, Lepidoptera and Nematodes, to the plants.

Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex (registered trademark) (a corn variety for expressing Cry1Fa2 toxin and phosphinotricine N-acetyl transferase (PAT) so as to confer tolerance to glufosinate), NuCOTN33B (registered trademark) (a cotton variety for expressing Cry1Ac toxin), Bollgard (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark). Agrisure (registered trademark) GT Advantage (GA21 glyphosate-tolerant trait), Agrisure (registered trademark) CB Advantage (Bt11 corn borer (CB) trait), and Protecta (registered trademark).

The aforementioned "plants" also include crops produced by using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor, among which KP1, KP4 and KP6 toxins produced by viruses have been known; stilbene synthase; bibenzyl synthase; chitinase; glucanase; a PR protein; and antipathogenic substances generated by microorganisms, such as a peptide antibiotic, an antibiotic having a hetero ring and a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, and so on.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soybean having reduced linolenic content) or high-lysine (high-oil) corn (corn with increased lysine or oil content).

Stack varieties are also included in which a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content are combined.

EXAMPLES

The present invention will be described in more detail by way of Formulation Examples, Treatment Examples and Test Examples, but the present invention is not limited only to the following Examples. In the following Examples, the part represents part by weight unless otherwise specified.

Formulation Example 1

Two (2) parts of the compound I and 8 parts of fipronil are dissolved in a mixture of 35 parts of xylene and 35 parts of N,N-dimethylformamide, to which 14 parts of polyoxyethylene styryl phenyl ether and 6 parts of calcium dodecylbenzene sulfonate are added, and the mixture is well stirred to give an emulsifiable concentrate.

Formulation Example 2

Ten (10) parts of the compound I and 10 parts of fipronil are added to a mixture of 4 parts of sodium lauryl sulfate, 2 parts of calcium lignin sulfonate, 20 parts of a synthetic hydrated silicon oxide fine powder and 54 parts of diatomaceous earth, and the mixture is stirred with a mixer to give a wettable powder.

Formulation Example 3

To 1 part of the compound I and 1 part of fipronil, 1 part of a synthetic hydrated silicon oxide fine powder, 2 parts of calcium lignin sulfonate, 30 parts of bentonite and 65 parts of kaolin clay are added, followed by well mixing with stirring. Then, a suitable amount of water is added to the mixture, which is further stirred, granulated with a granulator and then air-dried to give a granule.

Formulation Example 4

One (1) part of the compound I and 1 part of fipronil are dissolved in a proper amount of acetone, to which 5 parts of a synthetic hydrated silicon oxide fine powder, 0.3 parts of PAP and 92.7 parts of Fubasami clay are added, followed by well mixing with stirring. The removal of acetone by evaporation gives a dust formulation.

Formulation Example 5

Ten (10) parts of the compound I, 10 parts of fipronil, 35 parts of white carbon containing 50 parts of a polyoxyethylene alkyl ether sulfate ammonium salt, and 55 parts of water are mixed and the mixture is finely ground by a wet grinding method to give a flowable formulation.

Formulation Example 6

Dissolved are 0.1 part of the compound I and 1 part of fipronil in 5 parts of xylene and 5 parts of trichloroethane, followed by mixing with 88.9 parts of a deodorized kerosene to give an oil agent.

Treatment Example 1

To 12.5 parts of the compound I and 12.5 parts of fipronil, 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and rice seeds are soaked in the dilution for 24 hours until active ingredients are absorbed into the rice seeds to give treated seeds.

Treatment Example 2

Well mixed are 12.5 parts of the compound I and 12.5 parts of fipronil, 25 parts of clay for the formulation, 25 parts of polyvinyl alcohol containing 50 parts of SOLGEN TW-20, and 25 parts of water with stirring to give a material for forming pellets.

Then, cabbage seeds are embedded in the center of 20 mg of the material for forming pellets, followed by forming into spheres and further drying to give treated seeds.

Treatment Example 3

Mixed are 12.5 parts of the compound I and 12.5 parts of fipronil, 20 parts of white carbon containing 50% (weight) of a polyoxyethylene alkyl ether sulfate ammonium salt, and 55 parts of water, and finely ground by a wet grinding method to give a flowable formulation.

Cotton seeds are put in a stainless steel pot (having a volume of about 1,200 mL) equipped with a lifting blade for lifting seeds when the pot is rotated, and then the pot is inclined at an angle of about 45 degrees and mechanically rotated so that satisfactory mixing and tumbling granulating effect can be obtained in the pot.

The flowable formulation is diluted with water by 100 times and a hand sprayer is turned toward the inside of the pot, and then the dilution is directly sprayed to the center of a tumbling granulating layer of cotton seeds. Furthermore, the sprayer is stopped and low-pressure air is sprayed to seeds, and then the seed coating is immediately dried.

Thereafter, spraying using a hand sprayer is restarted. This spraying and drying cycle is repeated until a predetermined amount of a fluid suspension is applied to seeds, to give treated seeds.

Treatment Example 4

To 12.5 parts of the compound I and 12.5 parts of fipronil, 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and the dilution is sprayed onto a sugarcane stem cutting.

Test Example 1

In line with Formulation Example 5, compositions of the compound I and fipronil are prepared, and diluted with water so as to obtain predetermined concentrations (10, 50, 100 or 200 ppm of fipronil for 100 ppm of the compound I) of chemical solutions for test. Each of the compound I and fipronil is separately formulated into an emulsifiable concentrate, and diluted with water so as to obtain predetermined concentrations (10, 50, 100 or 200 ppm) of chemical solutions for test. Each of these test chemical solutions is irrigated to the foot of radish sprouts (on 7th days after germination) cultivated in a polyethylene cup, and the sprouts in the cup is stored at 25° C. As a control group, a dilution containing none of the active ingredients is applied in the same manner. After a few days, larvae of *Spodoptera litura* are released on the radish sprouts. After 2 days, the number of healthy radish sprouts is counted.

The result shows that the number of healthy radish sprouts in the group treated with both of the compound I and fipronil is obviously larger than those in the control group, the group treated with the compound I singly, and the group treated with fipronil singly.

Test Example 2

An aqueous solution of the compound I prepared by dissolving the compound I in water was appropriately mixed with a chemical solution of fipronil prepared by diluting Fipronil (Prince Flowable: manufactured by BASF Agro, Ltd.) with water to prepare a mixed chemical solution for test of the compound I and fipronil with a predetermined concentration. The foot of a rice seedling (2 weeks after germination) cultivated in a 90-ml plastic cup using cultivation soil was treated with 5 ml of the mixed chemical solution for test. After 3 days, 30 of first-instar larvae of *Pseudaletia Separata* were released per plant. After 3 days, the number of surviving larvae was counted and the control rate was calculated using the equation A.

For comparison, the test was conducted in the same manner using an aqueous solution for test having a predetermined concentration of the compound I prepared by diluting an aqueous solution of the compound I with water, and a chemical solution for test having a predetermined concentration of fipronil prepared by diluting a chemical solution of fipronil with water, respectively.

The results are shown in Table 1.

In the treatment with both of the compound I and fipronil, a greater control efficacy than that in the case of the treatment with the compound I or fipronil singly was observed.

$$\text{Control Rate}=100\times(1-[(Ts/30)/(Cs/30)]) \qquad \text{“Equation A”}$$

where Ts and Cs denote the number of surviving larvae in the treatment group and the non-treatment group, respectively. When the control rate is less than 0 (Ts>Cs), it is represented by 0.

TABLE 1

| Test compounds: Compound I Active ingredient concentration (ppm) | Test compounds: Fipronil Active ingredient concentration (ppm) | Control rate (%) |
|---|---|---|
| 10 | 10 | 77 |
| 10 | 30 | 77 |
| 10 | 100 | 86 |
| 30 | 10 | 77 |
| 30 | 30 | 82 |
| 30 | 100 | 86 |
| 100 | 30 | 82 |
| 100 | 100 | 86 |
| 10 | 0 | 0 |
| 30 | 0 | 0 |
| 100 | 0 | 0 |
| 0 | 10 | 23 |
| 0 | 30 | 41 |
| 0 | 100 | 68 |

Test Example 3

An aqueous solution of the compound I prepared by dissolving the compound I in water was appropriately mixed with a chemical solution of fipronil prepared by diluting fipronil (Prince Flowable: manufactured by BASF Agro, Ltd.) with water to prepare a mixed chemical solution for test of the compound I and fipronil with a predetermined concentration. In 40 ml of the mixed chemical solution for test, 100 of rice seeds were immersed and allowed to stand at 30° C. for 24 hours, and then each of the 15 seeds were sown in cultivation soil filled in a 90-ml plastic cup. Eleven (11) days after the sowing, 30 of first-instar larvae of *Nilaparvata lugens* were released on seedlings germinated from the rice seeds. After 7 days, the number of the surviving larvae was counted and the control rate was calculated using the equation A in the same manner as in Example 2.

For comparison, the test was conducted in the same manner using an aqueous solution for test having a predetermined concentration of the compound I prepared by diluting an aqueous solution of the compound I with water, and a chemical solution for test having a predetermined concentration of fipronil prepared by diluting a chemical solution of fipronil with water, respectively.

The results are shown in Table 2.

In the treatment with both of the compound I and fipronil, a greater efficacy than that in the case of the treatment with the compound I or fipronil singly was observed.

TABLE 2

| Test compounds | | |
|---|---|---|
| Compound I Active ingredient concentration (ppm) | Fipronil Active ingredient concentration (ppm) | Control rate (%) |
| 50 | 3.1 | 82 |
| 200 | 3.1 | 80 |
| 50 | 0 | 11 |
| 200 | 0 | 21 |
| 0 | 3.1 | 50 |

Industrial Applicability

According to the present invention, a composition for controlling pests having excellent control efficacy for pests and a method effective for controlling pests can be provided.

The invention claimed is:

1. A composition for controlling pests comprising, as active ingredients, 4-oxo-4-[(2-phenylethyl)amino]-butyric acid and fipronil.

2. The composition for controlling pests according to claim 1, wherein a weight ratio of 4-oxo-4-[(2-phenylethyl)amino]-butyric acid to fipronil is in the range of 1:99 to 99:1.

3. A seed treatment agent comprising, as active ingredients, 4-oxo-4-[(2-phenylethyl)amino]-butyric acid and fipronil.

4. A plant seed treated with effective amounts of 4-oxo-4-[(2-phenylethyl)amino]-butyric acid and fipronil.

5. A method of controlling pests, which comprises applying effective amounts of 4-oxo-4-[(2-phenylethyl)amino]-butyric acid and fipronil to a plant or growing site of plant.

6. The method of controlling pests according to claim 5, wherein the plant is seed or seedling.

7. The method of controlling pests according to claim 5, wherein the plant is a sugarcane stem cutting.

8. The method of controlling pests according to claim 5, wherein the growing site of plant is soil before or after planting the plant.

* * * * *